US00PP27353P3

(12) United States Plant Patent
Harvey

(10) Patent No.: US PP27,353 P3
(45) Date of Patent: Nov. 8, 2016

(54) ***ORIGANUM* PLANT NAMED 'BELLISSIMO'**

(50) Latin Name: ***Origanum* hybrid**
Varietal Denomination: Bellissimo

(71) Applicant: Marcus Harvey, South Hobart (AU)

(72) Inventor: Marcus Harvey, South Hobart (AU)

( * ) Notice: Subject to any disclaimer, the term of this patent is extended or adjusted under 35 U.S.C. 154(b) by 17 days.

(21) Appl. No.: 14/544,685

(22) Filed: Feb. 3, 2015

(65) Prior Publication Data

US 2016/0227690 P1 Aug. 4, 2016

(51) Int. Cl.
*A01H 5/02* (2006.01)

(52) U.S. Cl.
USPC ..... Plt./258

(58) Field of Classification Search
USPC ..... Plt./263.1, 258
See application file for complete search history.

(56) References Cited

PUBLICATIONS

Janna Schreier Garden Design/London (https://jannaschreier.com/2014/12/15/brand-new-plant-releases-2014/). 6 pages.*
(Southern Australian Garden and Outdoor Living vol. 13, p. 6 (https://issuu.com/gardenandoutdoorliving/docs/sagol_13_lo_res). 2 pages.*

* cited by examiner

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Origanum* cultivar named 'BELLISSIMO' is disclosed, characterized by a controlled, attractive, dome shaped growth habit. Flowers have large dark pink floral bracts. The new cultivar is an *Origanum*, typically suited for garden and ornamental container use.

2 Drawing Sheets

Latin name of the genus and species: *Origanum* hybrid.
Variety denomination: 'BELLISSIMO'.

BACKGROUND OF THE INVENTION

The new cultivar is a product of a planned breeding program. The new variety originated from the pollination of the seed parent, an unpatented variety of *Origanum* hybrid known as 'Kent Beauty' with the pollen parent, an unpatented variety of *Origanum* hybrid known as 'Barbara Tingey' conducted by the inventor during 2009. The crossing was made in a commercial nursery in South Hobart, Tasmania, Australia.

'BELLISSIMO' was first discovered by the inventor, Marcus Harvey, in 2010 at the same nursery in South Hobart, Australia. The inventor observed the new variety for three years, making the final selection of the variety during 2013.

Asexual reproduction of the new cultivar 'BELLISSIMO' was first performed in the nursery at South Hobart, Australia by vegetative tip cuttings during 2010. 'BELLISSIMO' has since produced at least six generations and has shown that the unique features of this cultivar are stable and reproduced true to type.

SUMMARY OF THE INVENTION

The cultivar 'BELLISSIMO' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Bellissimo'. These characteristics in combination distinguish 'BELLISSIMO' as a new and distinct *Origanum* cultivar:

1. Controlled, attractive dome shaped plant habit.
2. Deep pink bract coloration

PARENTAL COMPARISON

Plants of the new cultivar 'BELLISSIMO' are similar to the female parent 'Kent Beauty' in most horticultural characteristics. However, 'BELLISSIMO' differs in producing bracts of a much deeper pink color than the seed parent.

Plants of the new cultivar 'BELLISSIMO' are similar to the male parent 'Barbara Tingey' in most horticultural characteristics. However, plants of 'BELLISSIMO' are dome shaped in habit, whereas plants of the pollen parent are prostrate to trailing.

COMMERCIAL COMPARISON

'BELLISSIMO' can be compared to *Origanum laevigatum* 'Lizzie', unpatented. Plants are similar in most horticultural characteristics, however, the new variety differs in the following:

1. The new variety has wider inflorescence
2. The new variety has deeper pink colored bracts.
3. Plants of the new variety are more mounding and compact than plants of this comparator.

'BELLISSIMO' can be compared to *Origanum laevigatum* 'Pilgrim', unpatented. Plants are similar in most horticultural characteristics, however, the new variety differs in the following:

1. The new variety has a much wider inflorescence.
2. Plants of the new variety are mounding and compact, plants of this comparator are upright and approximately 80% taller than plants of 'Bellissimo'.

BRIEF DESCRIPTION OF THE PHOTOGRAPHS

Figure 1:
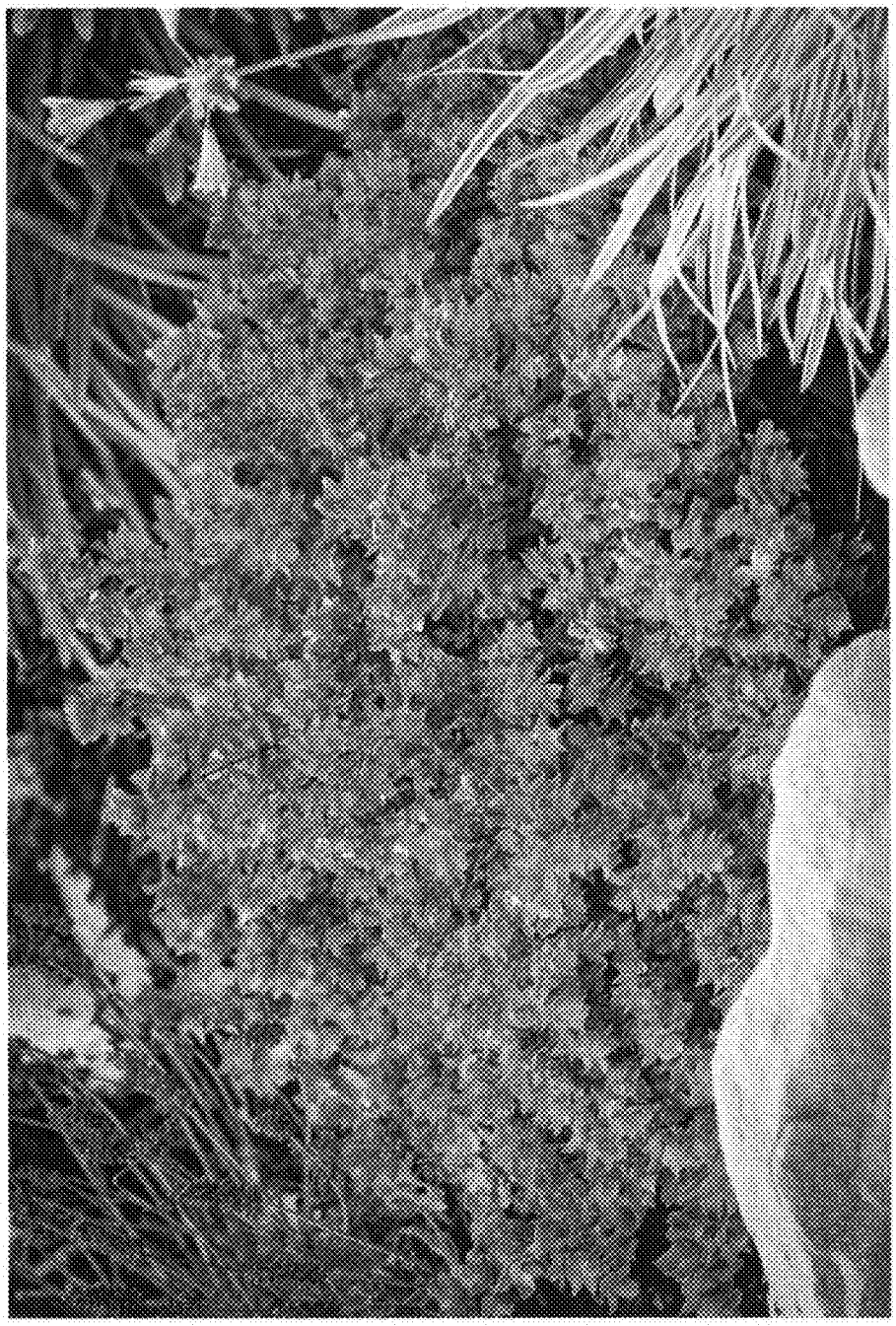

The accompanying photograph in FIG. 1 illustrates in full color a typical plant of 'BELLISSIMO' grown outdoors in South Hobart, Australia. This plant is approximately 1 year old, shown growing in the ground.

Figure 2:
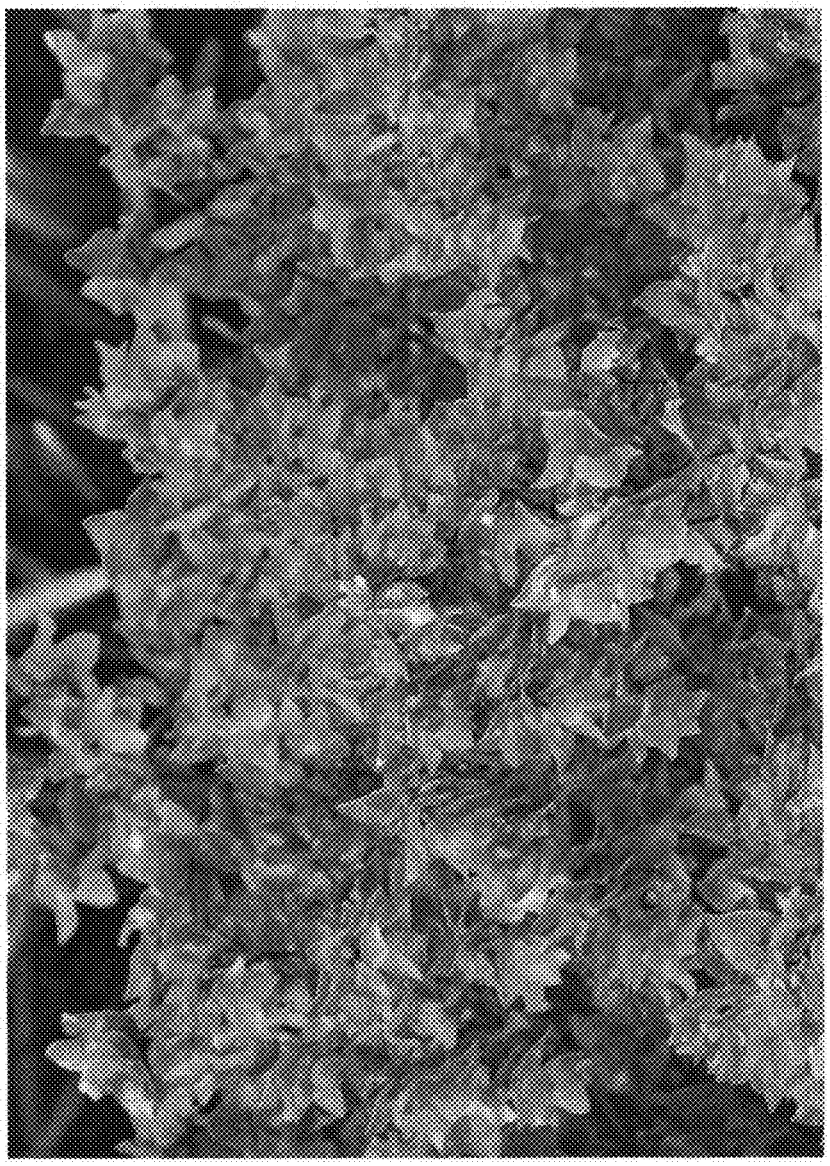

FIG. 2 illustrates a close up view of the floral bracts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BELLISSIMO' plants grown in a outdoors in South Hobart, Australia. Temperatures ranged from 5° C. to 18° C. at night and approximately 10° C. to 30° C. during the day. No artificial light, photoperiodic treatments or chemical treatments were given to the plants. Measurements and numerical values represent averages of typical plant types.

Botanical classification: *Origanum* hybrid 'Bellissimo'.

Age of the plant described: Approximately 1 year.

Container size of the plant described: Approximately 2 liter pot.

PROPAGATION

Time to initiate roots: About 5 days at temperatures of 20 to 25 degrees C.

Time to develop roots: About 20 days at temperatures of 20 to 25 degrees C.

Root color: Youngest roots and root hairs near RHS White 155A mature roots near Brown 200B.

Root description: Very thin and fibrous.

PLANT

Growth habit: Fleshy annual or tender perennial, forming an even dome shape.

Height: Measured from top soil line of pot, approximately 28 cm to top of highest leaf. Approximately 35 cm to top of highest inflorescence.

Plant spread: Approximately 45 cm.

Growth rate: Rapid.

Branching characteristics: Very well branched. Approximately 20 to 30 branches.

Length of primary branches: About 30 cm.

Diameter of primary branches: About 0.3 cm.

Characteristics of primary lateral branches:

- *Form*.—Cylindrical.
- *Diameter*.—About 0.3 cm.
- *Color*.—Near RHS Green 143A.
- *Texture*.—Pubescent.
- *Strength*.—Strong, flexible.

Internode length: Average range about 1.3 to 2.0 cm.

FOLIAGE

Leaf:

- *Arrangement*.—Simple; opposite.
- *Average length*.—Approximately 1.9 cm.
- *Average width*.—Approximately 1.4 cm.
- *Shape of blade*.—Ovate to somewhat deltate.
- *Apex*.—Acute.
- *Base*.—Blunt.
- *Margin*.—Entire.
- *Texture of top surface*.—Pubescent, matte.
- *Texture of bottom surface*.—Pubescent, matte.
- *Quantity of leaves per branch*.—Approximately 15.
- *Color*.—Young foliage upper side: Near RHS Green 137A. Young foliage under side: Near RHS Green 137A. Mature foliage upper side: Near RHS Green 137A. Mature foliage under side: Near RHS Green 137A.
- *Venation*.—Type: Pinnate. Venation color upper side: Near RHS Yellow-Green 144A. Venation color under side: Near RHS Yellow-Green 144A.

Petiole: Not present, sessile.

FLOWER

Natural flowering season: Spring and Summer. Flowering begins late Spring and continues until Fall.

Inflorescence:

- *Form*.—Axillary, compact cyme, large, ornamental bracts.
- *Width of entire inflorescence*.—Approximately 5 cm.
- *Height of entire inflorescence*.—Approximately 9 cm.
- *Quantity of individual flowers in inflorescence*.—Average range 10 to 15.

Quantity of inflorescence per plant: Average range 20 to 50.

Persistent or self-cleaning: True flowers self-cleaning, bracts persistent.

Peduncle:

- *Length*.—Approximately 3.5 cm.
- *Width*.—Approximately 0.3 cm.
- *Color*.—Near RHS Yellow-Green 144B.
- *Texture*.—Pubescent.
- *Strength*.—Flexible.

Flowers:

- *Size*.—Diameter: Approximately 0.4 cm. Length: Approximately 0.6 cm.

Fragrance: Moderately strong herbal scent.

Corolla:

- *Petal arrangement*.—The corolla is sympetalous and typically bilabiate with 2 small, fully fused lobes forming a single upper lip and 3 larger fused lobes forming a lower lip.
- *Margin*.—Entire.
- *Tip shape*.—Upper lip tip obtuse, lower lip tip retuse.
- *Length*.—Upper lip Approximately 0.1 cm. Lower lip Approximately 0.2 cm. Tube length Approximately 0.4 cm.
- *Width*.—Upper lip: Approximately 0.3 cm, lower lip Approximately 0.2 cm. Tube width: Approximately 0.2 cm.
- *Texture*.—Glabrous all surfaces.

Color: Upper Lip:

*When opening*.—Inner surface: Near RHS Purple-Violet N81D. Outer surface: Near RHS Purple-Violet N81A, very slightly flushed Purple N79A.

*Fully opened*.—Inner surface: Near RHS Purple-Violet N81D. Outer surface: Near RHS Purple-Violet N81A.

*Fading*.—Inner surface: Near RHS Violet 84D, flushed Purple-Violet N81A. Outer surface: Near RHS Purple 77A.

Color: Lower Lip:

*When opening*.—Inner surface: Near RHS Purple N78A. Outer surface: Near RHS Purple N78A.

*Fully opened*.—Inner surface: Near RHS Purple N78A. Outer surface: Near RHS Purple N78B.

*Fading*.—Inner surface: Near RHS Red-Purple 72A. Outer surface: Near RHS Purple 77A.

Color: Tube:

*When opening*.—Inner surface: Near RHS Purple-Violet N81C, streaked Violet 84D. Outer surface: Near RHS Purple-Violet N80A.

*Fully opened*.—Inner surface: Near RHS Purple-Violet N80B. Outer surface: Near RHS Purple-Violet N81A.

*Fading*.—Inner surface: Near RHS Purple 75D, lightly streaked Purple N78B. Outer surface: Near RHS Purple N78A.

Calyx:

*Length*.—Approximately 0.2 cm.

*Diameter*.—Approximately 0.1 cm.

*Shape*.—Tubular.

Sepals:

*Shape*.—Quantity per flower: 3, fused to form a tube. Unfused apex.

*Length*.—Approximately 0.1 cm unfused portion.

*Width*.—Approximately 0.1 cm.

*Margin*.—Entire.

*Apex*.—Acute.

*Texture*.—Softly pubescent and ridged.

*Color*.—Immature: Near RHS Green 138B. Mature: Near RHS Green 138B.

Bud:

*Shape*.—Deltate.

*Length*.—0.6 cm.

*Diameter*.—0.3 cm.

*Color*.—Near RHS Red-Purple 61A.

Bracts:

*Quantity*.—Average 2.

*Arrangement*.—Opposite.

*Length*.—Approximately 1.6 cm.

*Width*.—Approximately 0.9 cm.

*Shape*.—Deltate.

*Apex*.—Acute.

*Base*.—Oblique.

*Margin*.—Entire.

*Texture*.—Glabrous.

*Appearance*.—Slightly shiny.

*Color*.—Inner Surface: Near Red-Purple 60D. Outer surface: Near Red-Purple 60C.

REPRODUCTIVE ORGANS

Reproductive organs significantly reduced and malformed. True sterility is unknown.

OTHER CHARACTERISTICS

Seeds: Seed production not observed.

Disease/pest resistance: Neither resistance nor susceptibility to common diseases and pets of *Origanum* have been observed in the new variety.

Temperature tolerance: Tolerates temperatures from approximately 4° C. to 38° C.

What is claimed is:

1. A new and distinct cultivar of *Origanum* hybrid plant named 'BELLISSIMO' as herein illustrated and described.

* * * * *